(12) United States Patent
Riordan et al.

(10) Patent No.: US 7,887,501 B2
(45) Date of Patent: Feb. 15, 2011

(54) COMPRESSIVE HEAD DRESSINGS AND ASSOCIATED METHODS

(76) Inventors: John P. Riordan, 4408 Gladwood Pl., Lynchburg, VA (US) 24503; Chris M. Thomson, 212 Meredith Pl., Lynchburg, VA (US) 24506

(*) Notice: Subject to any disclaimer, the term of this patent is extended or adjusted under 35 U.S.C. 154(b) by 45 days.

(21) Appl. No.: 12/155,309

(22) Filed: Jun. 2, 2008

(65) Prior Publication Data
US 2009/0299254 A1   Dec. 3, 2009

(51) Int. Cl.
*A61F 13/12* (2006.01)
*A61L 15/00* (2006.01)

(52) U.S. Cl. .......... 602/74; 424/445

(58) Field of Classification Search ......... 424/443–449; 602/74, 53, 63, 69, 71; 2/209.11
See application file for complete search history.

(56) References Cited

U.S. PATENT DOCUMENTS

| | | | |
|---|---|---|---|
| 649,896 A | 5/1900 | Baughman | |
| 3,709,225 A * | 1/1973 | Sobel | 604/303 |
| 4,937,885 A * | 7/1990 | Gregg | 2/209.11 |
| 5,031,609 A | 7/1991 | Fye | |
| 5,489,262 A * | 2/1996 | Cartmell et al. | 602/57 |
| 5,779,657 A | 7/1998 | Daneshvar | |
| 6,592,535 B2 | 7/2003 | Ravikumar | |
| 6,762,337 B2 | 7/2004 | Boukanov et al. | |
| 7,329,792 B2 | 2/2008 | Buckman et al. | |
| 2002/0103520 A1 | 8/2002 | Latham | |
| 2002/0142027 A1 | 10/2002 | Gueret | |
| 2003/0199922 A1 | 10/2003 | Buckman | |
| 2004/0241215 A1 | 12/2004 | Lipman | |
| 2005/0027227 A1 | 2/2005 | Dumas et al. | |
| 2005/0273071 A1 | 12/2005 | McKiernan et al. | |
| 2006/0094995 A1 | 5/2006 | Bauer | |
| 2006/0135319 A1 | 6/2006 | Berman | |
| 2006/0204738 A1 | 9/2006 | Dubrow et al. | |
| 2006/0206047 A1 | 9/2006 | Lampe et al. | |
| 2006/0229662 A1 | 10/2006 | Finkielsztein et al. | |
| 2006/0247564 A1 | 11/2006 | Ravikumar | |
| 2006/0281912 A1 | 12/2006 | James et al. | |
| 2007/0042025 A1 * | 2/2007 | Gladman et al. | 424/445 |
| 2007/0060856 A1 * | 3/2007 | Spearman et al. | 602/48 |
| 2007/0130840 A1 | 6/2007 | Jouhannet | |
| 2007/0163024 A1 | 7/2007 | Kuehn | |
| 2007/0255243 A1 | 11/2007 | Kaun et al. | |
| 2008/0032920 A1 | 2/2008 | Prestwich et al. | |
| 2008/0125688 A1 * | 5/2008 | Kellogg et al. | 602/61 |

OTHER PUBLICATIONS

Belman et al., From the Battlefield to the Street—Experience of a Suburban Fire/EMS Agency with Chitosan Dressing, Emergency Medicine & Critical Care Review, 2006, pp. 46-47.

* cited by examiner

*Primary Examiner*—Patricia M Bianco
*Assistant Examiner*—Ophelia Hawthorne
(74) *Attorney, Agent, or Firm*—Oliff & Berridge, PLC

(57) ABSTRACT

A compressive dressing and method allow quick, simple and effective treatment of head trauma by cinching and, optionally, an elastomeric layer.

30 Claims, 4 Drawing Sheets

ANTERIOR VIEW

LATERAL VIEW

COMPRESSIVE HEAD DRESSINGS AND ASSOCIATED METHODS

TECHNICAL FIELD

This disclosure is directed to devices and methods to stabilize traumatic scalp wounds, thus facilitating hemostasis in a sequential, controlled manner.

BACKGROUND

Scalp lacerations are a frequent result of head trauma. A scalp laceration may be an isolated injury and the sole factor for an emergency department visit or an important component of multiple injuries to the scalp and/or other portions of the body. The scalp is highly vascular and even seemingly minor lacerations can lead to profound blood loss which, if unrecognized, can result in shock. Excessive bleeding exposes health care providers and bystanders to blood-borne pathogens and may, at the scene of the trauma, cause panic. The prevalence of patients taking blood thinners, worsens blood loss in this population. A method to control hemorrhage is needed.

Hemorrhagic scalp wounds are common. These injuries occur in many contexts, including (1) secondary to isolated head and scalp trauma, such as in, for example, falls, industrial accidents, and sports; (2) associated with multi-system trauma, such as, for example, motor vehicle accidents, falls, industrial accidents and assaults; (3) in nursing homes from ground-level falls and falls from bed; and (4) in the military combat and training setting. In the civilian population, even among seemingly healthy and active individuals, the problem is compounded by the increasing use of anticoagulants, which potentially transform seemingly innocuous scalp wounds into serious hemorrhagic events worthy of immediate and effective attention.

Particularly in the emergency setting, quick and simple action must be taken to minimize or stop blood loss. Existing stabilization measures are inadequate, the most common of which is direct pressure. This is applied by the patient, a bystander, or pre-hospital provider. In many emergency settings, including ambulance and helicopter transfer, few emergency practitioners are available. Dedicating a practitioner or other individual to applying such pressure can keep that person from performing many other emergency duties, and often effective pressure application is not achieved. It is often the case that, by the time emergency transport from an accident scene is complete, significant blood loss has occurred. The problem may be compounded in the hospital when, in an attempt to manage associated life-threatening injuries, the patient is taken for extensive diagnostic testing and treatment before definitive wound closure.

U.S. Pat. No. 6,592,535 describes an apparatus for arresting scalp bleeding. U.S. Pat. No. 6,592,535 describes a skull cap having a plurality of inflatable bladders, in which the inflated bladders exert pressure on the bleeding scalp and result in hemostasis. The skull cap is fastened about the victim's skull by attaching overlapping lobes with a VELCRO strap.

U.S. Pat. No. 6,762,337 describes a series of pressure bandages for wounds in a packaged and hermetically sealed form. U.S. Pat. No. 6,762,337 describes a dome-shaped pressure bandage with a bladder and gauze liner and gas cartridge in a pouch for filling the bladder and a hook strap and loop strap for securing the bandage to the victim's head.

Neither U.S. Pat. No. 6,592,535 nor U.S. Pat. No. 6,762,337, however, solve the problem of treating head trauma both in cases where there is an identified wound and in cases where there is also an unidentified wound in a simple and effective manner without causing substantial movement or reconfiguration of the patient during application and removal of the bandage. Both systems are complex and thus time consuming and subject to failure.

SUMMARY

Compressive dressings of the invention will control scalp hemorrhage by providing a substantially uniform compressive force to the scalp. Embodiments can provide substantially uniform compression to temporize bleeding from lacerations that are: (1) difficult to find, and (2) oriented in any direction, stellate, or constitute partial avulsions. Embodiments are easily applied, removed and replaced so health care providers can examine a wound and provide hemorrhage control prior to, during, between and/or after other treatments with minimal movement of the patient's head.

Designed by emergency physicians with extensive experience in the trauma setting, embodiments of this simple, efficient device apply a compressive force substantially uniformly to the entire scalp. In embodiments, compressive dressings of the invention allow hemostasis of single or multiple lacerations in any orientation, allowing health care providers to focus on other injuries while limiting blood loss.

BRIEF DESCRIPTION OF THE DRAWINGS

Various exemplary embodiments of disclosed devices and methods for treating head trauma are schematically depicted in the following drawings, wherein.

DETAILED DESCRIPTION OF EMBODIMENTS

Figure 1A:
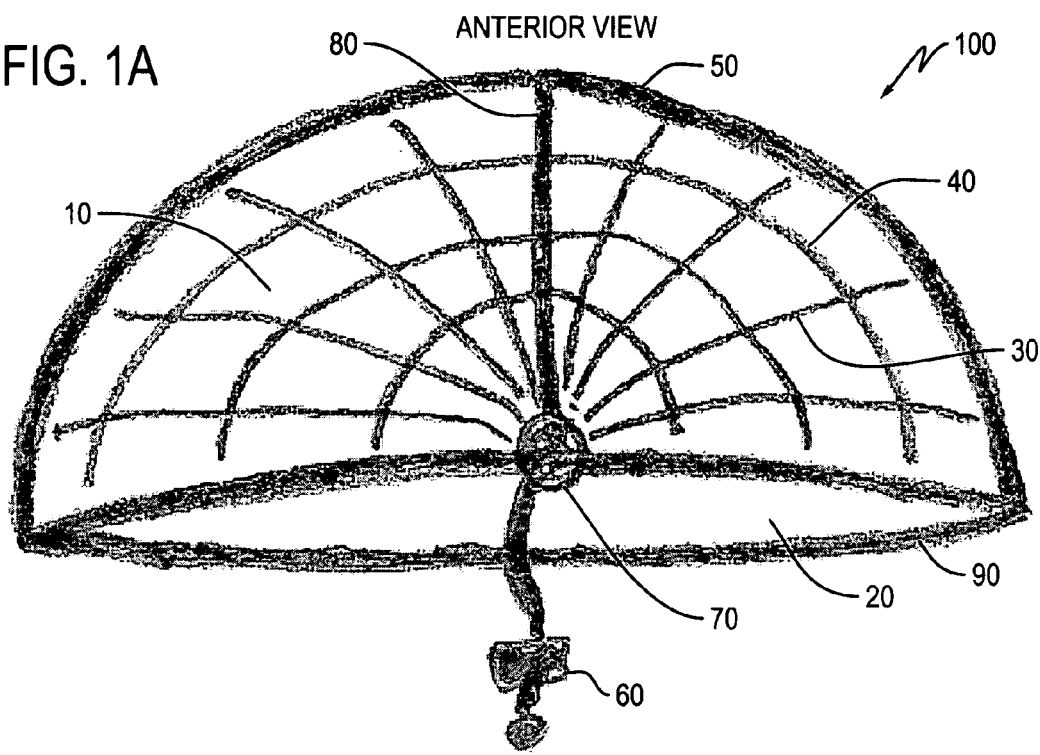
FIGS. 1A and 1B are respectively an anterior view and a lateral view of an embodiment of a compressive dressing.

In the drawings, like reference numerals have been used throughout to designate like elements.

For purposes of this disclosure, the term hemostasis is defined as the stoppage of bleeding or hemorrhage.

For purposes of this disclosure, the term cinchable is defined as the quality of being able to be tightened.

For purposes of this disclosure, the term scalp is defined as the portion of the head approximating the area where hair is usually present on the human head, regardless of whether an individual patient has hair or is bald at that portion of the head.

Compressive dressings of the invention may be particularly useful in pre-hospital civilian and military settings, when rapid control of scalp hemorrhage during transport to definitive care will allow the pre-hospital provider to perform other actions without having to apply continuous pressure to the scalp. They may be useful in the emergency department setting to limit blood loss as a diagnostic workup is performed prior to definitive scalp repair. Nursing homes may find them useful for scalp-traumatized residents. They may also find use in discharged patients where a simple, compressive head dressing is required, as well as in many other settings.

Compressive head dressings in embodiments of the invention are easy to use and effective, which is particularly important in pre-hospital phases, such as, for example, during ground and/or air transport from an accident or crime scene to a hospital, clinic or other care facility. The compressive dressing may also play a significant role as a surgical tool for practitioners while treating patients on-site at the hospital during all phases of patient care, such as, for example, during operating or emergency surgical procedures either during transport from various rooms within the hospital or as a device to control hemorrhaging during various operating procedures or as a post-operative recovery device. Such compressive dressings may also be useful in various out-patient contexts, such as, for example, nursing home facilities, or any context in which head trauma may occur, e.g., athletic sites or even in the home, as well as in military, industrial and other potentially dangerous settings. In these and other contexts, the compressive dressings may provide an immediate and critical response to head trauma that satisfies the long-felt need for a device capable of providing the compressive force appropriate to easily and efficiently control or terminate hemorrhaging before serious or fatal damage. Embodiments also permit easy and efficient control or termination of hemorrhaging from scalp lacerations that are difficult to localize due to being obscured by hair, presence of copious blood and clot on the scalp, darkness of the environment, size and other reasons.

Embodiments provide for a compressive dressing for treating head trauma comprising one or a plurality of layers that cover at least a scalp portion of a head; and at least one tightener, wherein the at least one tightener is configured to cinch at least one layer to provide a substantially uniform compressive force over a scalp of the head.

Embodiments provide for a compressive dressing for treating head trauma comprising at least one absorptive or non-absorptive inside layer that contacts the head. Some embodiments include at least one elastomeric layer configured to provide an additional substantially uniform compressive force around the head such that a bi-phasic application of force occurs—one phase from the elastomeric layer and one phase from the cinchable layer. Embodiments include at least one filament, preferably a plurality of filaments, more preferably a plurality of filaments formed into a matrix, as the cinchable layer, and at least one tightener. The filament layer may optionally be formed over the optional at least one inside layer and/or the optional at least one elastomeric layer, and may be moved and/or tensioned by the at least one tightener to provide a substantially uniform compressive force around the head.

Embodiments provide methods for treating head trauma comprising covering at least a portion of a head with a compressive dressing including at least one layer, such as a dressing as described above and elsewhere herein; and cinching the at least one layer with a tightener to provide a substantially uniform compressive force against the head over the scalp.

Embodiments provide a method for treating head trauma comprising covering at least a portion of a head with a compressive dressing comprising an elastomeric layer that applies a first substantially uniform compressive force to the scalp; and cinching a matrix formed by at least one lateral filament and at least one longitudinal filament that converge at at least one tightener to apply a substantially uniform second compressive force over the scalp.

Figure 1B:
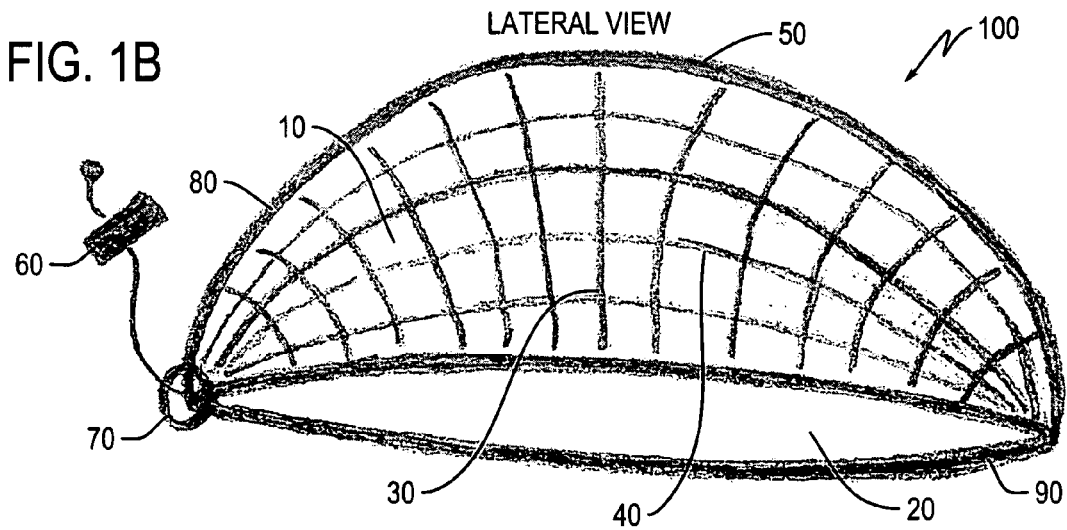

As shown in connection with the embodiment of FIGS. 1A and 1B, compressive dressing 100 may be a hat or cap-like structure for fitting over a patient's head to cover the scalp. It may include on the outside optional cover structure 50, to be discussed in further detail below, and has a hollow inner space 20 for surrounding the patient's head. Filaments such as lateral filaments 30 and longitudinal filaments 40 may together form a matrix 10. Some or all of the lateral filaments 30 and longitudinal filaments 40 may be directly or indirectly connected and may be separately or jointly controlled by the tightener 60. The tightener 60 provides a compressive force by allowing tightening of, and holding taut, the lateral filaments 30 and/or longitudinal filaments 40, for example by allowing such filaments to be pulled by an external force or a plurality of multiple forces that, individually or in combination, may act on some or all of the filaments.

Figure 1C:
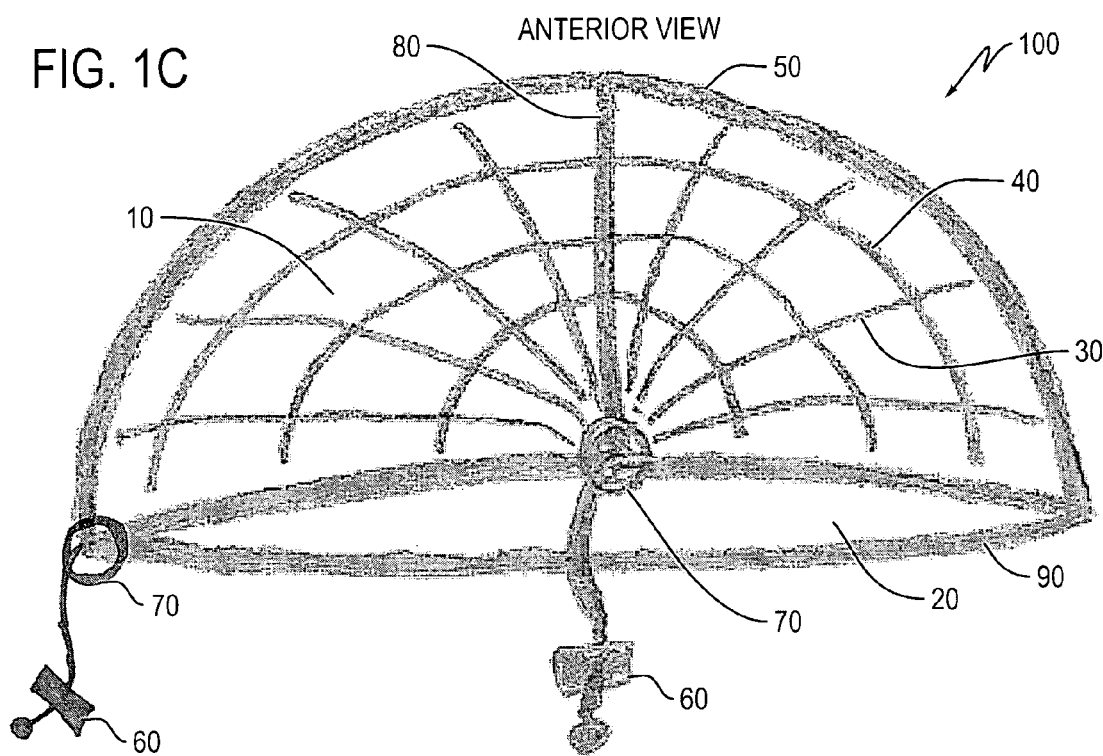
FIGS. 1C and 1D are respectively an anterior and a lateral view of an alternative embodiment of a compressive dressing.
Figure 1D:
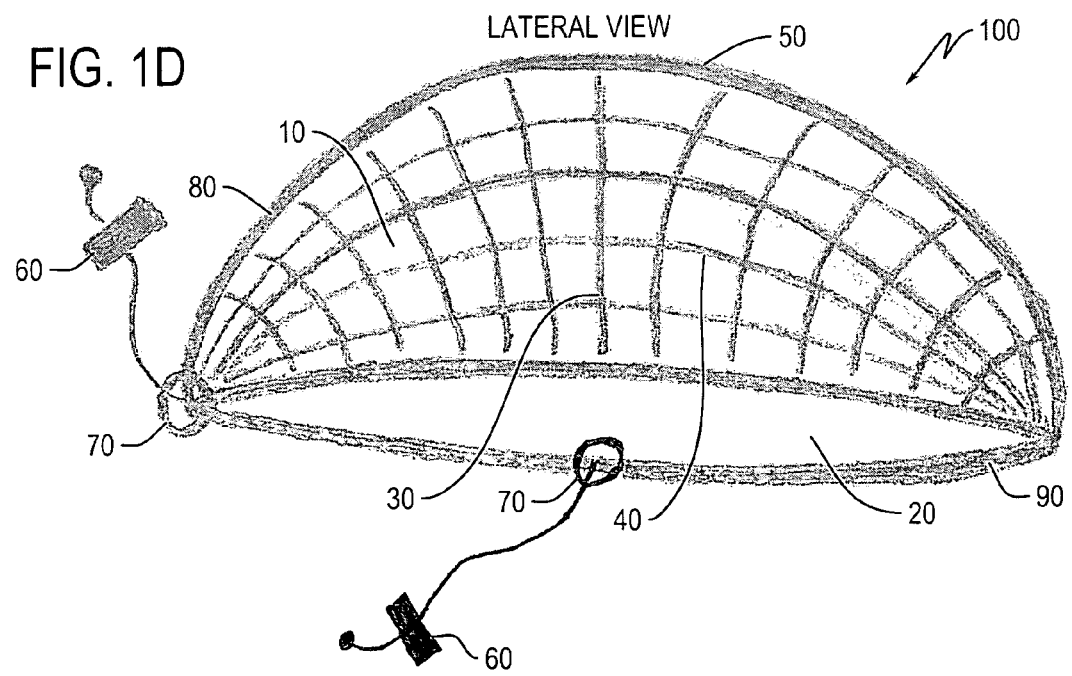

As shown in FIGS. 1A and 1B, the tightener 60 may be located at an anterior portion of a compressive dressing 100 on the patient's head. However, the tightener 60 is not limited to this location and may be located at any position on the compressive dressing 100. In embodiments, compressive dressing 100 may be placed in any orientation on the patient's head such that the location of the tightener 60 is variable. The compressive dressing 100 may be equipped with a plurality of tighteners, as appropriate, for the specific design of the cap. For example, as shown in FIGS. 1A and B, a tightener 60 may be located on the anterior portion of the compressive dressing 100 as it rests on the patient's head, but one or more tightener may also or alternatively be located at the posterior portion, either lateral side, the top, or any combination thereof on the compressive dressing 100. The versatility of the placement of the tightener 60 promotes versatile use of the cap in specific injury situations. For example, in the event that the front of the head is not readily accessible without unacceptable movement of the patient, embodiments may include a compressive dressing with a tightener located on the posterior portion of the compressive dressing. In embodiments, separate tighteners may for example be respectively provided for the lateral and longitudinal filaments, as shown in, for example, FIGS. 1C and 1D.

Figure 2:
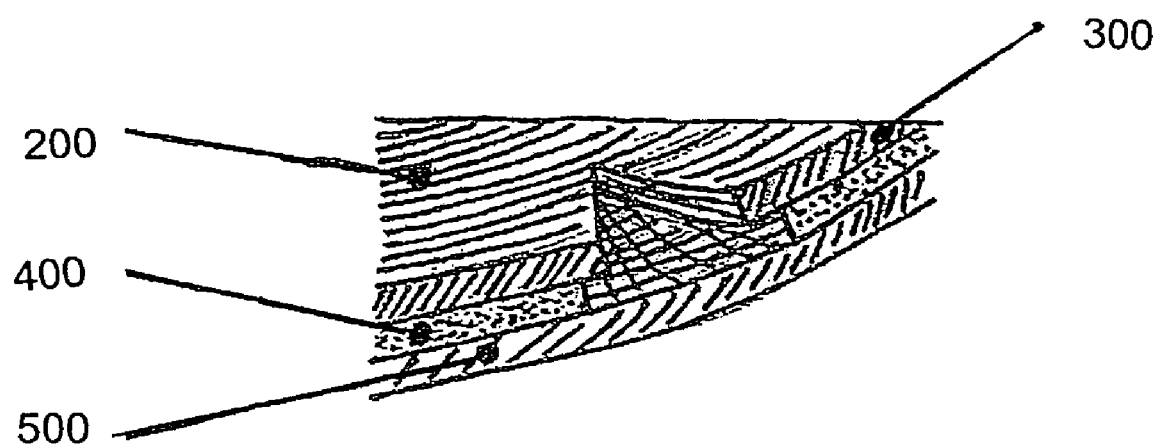
FIG. 2 is a cross-sectional view of a portion of an embodiment of a compressive dressing.

As shown in FIG. 2, the compressive dressing may comprise multiple layers. In the embodiment depicted in FIG. 2, the dressing comprises an inner layer 200, a matrix layer 400, and optionally, a protective layer 500. One or more of these layers may also be laminated structures. For example, inner layer 200 may be a laminate of an absorptive layer and an elastomeric layer 300.

Inner layer 200 may have any one or more of several qualities specific to the use of the compressive dressing. In embodiments, the inner layer 200 may treated with a hemostatic substance that may facilitate the slowing of bleeding resulting from traumatic injury to the patient's head and achieve hemostasis. The inner layer 200 may also be treated with other substances such as antibiotics, analgesics, moisturizers, and disinfectants. The treatment of the inner layer 200 is not limited to these substances and may also include, for example, various medications or ointments.

Examples of hemostatic substances include, but are not limited to: HemCon, QuickClot, BioHemostat, TraumaDex, Fibrin, Antifibrinolytics, and Tranexamic Acid.

The inner layer 200 may optionally be absorbent and/or be treated with absorbency enhancers. As an example, an absorbent inner layer 200 may be a gauze-type material. However, any suitable absorbent or non-absorbent material or enhancer is envisioned. Suitable materials include, but are not limited to: foams, gels, hydrocolloids, sponges, and cotton.

In embodiments, the compressive dressing 100 may have a filament layer such as matrix layer 400 that is cinchable. Matrix 10 may alone, or in combination with other materials, may make up layer 400. Layer 400 is preferably cinchable substantially uniformly around the patient's head. An external force applied in conjunction with the tightener may be used to cinch the compressive dressing 100 around the patient's head. As shown in FIGS. 1A and 1B, lateral filaments 30 and longitudinal filaments 40 form the matrix 10. Cinching may occur by an external force, such as a force exerted by the patient or a practitioner, pulling on leads extending from either or both of the lateral filaments 30 and longitudinal filaments 40 of the matrix 10. By applying an external pulling force to the leads, filaments are pulled taut in one or the other of, or simultaneously in, the lateral and longitudinal directions so as to create a substantially uniform compressive force over the scalp. Once the desired compressive force is achieved, the leads and/or filaments are held by the tightener 60 to maintain the substantially uniform compressive force established by cinching. At an appropriate time, such as after arriving at the hospital, the dressing may be easily removed by releasing the tightener 60.

The tightener 60 may be of a number of different types now known or hereafter developed. The mechanism of tightener 60 can be as simple as a spring operated mechanism for cinching a plurality of filaments by "pinching" leads and/or filaments against a surface(s). It is also envisioned that the tightener may operate automatically or mechanically such as by, for example, a cinch operated by an electronic motor or spring or by hand for rolling leads and/or filaments around a coil to tighten the matrix. Preferably, the tightener may be tightened to and released from a cinched condition with minimal movement of the patient.

The tightener 60 cinches filaments around the head of the patient to effectuate a substantially uniform compressive force. In embodiments, the matrix loosely fits around the patient's head upon the compressive dressing first being applied to the patient's head and before cinching. Once applied to the patient's head, in exemplary embodiments, the practitioner or patient, for example, cinches the filaments for both a better fit of the compressive dressing and to apply a compressive force, as appropriate. Alternatively, an elastomeric layer 300 may provide an initial compressive force, which is supplemented by force applied by cinching.

The leads may be the ends of each lateral filament 30 and longitudinal filament 40. Alternatively, in exemplary embodiments, at least some of the lateral filaments 30 and longitudinal filaments 40 may be considered "minor" filaments and may feed into a major lateral filament and major longitudinal filament 80 that forms a lead. In embodiments, a major perimeter filament 90 surrounds the patient's head around the base of the compressive dressing and is the filament to which all lateral filaments 30 feed and are attached, for example, by a stitch. A major longitudinal filament 80 may be located at either the anterior or posterior part of the head, to be co-located with the tightener, and be a filament into which each longitudinal filament feeds and is attached. In embodiments, the perimeter filament 90 and major longitudinal filament 80 pass through opening 70 in the cover structure 50, as shown in FIG. 1, and may be pulled by the external force to act on the matrix 10. In this manner, a force on the perimeter and major longitudinal filaments applies a substantially equal force to each minor filament thus creating a substantially uniform compressive force over the scalp.

The filaments described thus far may be composed of any suitable material. For example, the filaments may be natural and/or polymer-based single or multi-component monofilaments, threads or yarns. They may optionally be elastomeric.

In embodiments, compressive dressing 100 may also optionally contain an elastomeric layer 300. The elastomeric layer 300 may have any one or more of several qualities specific to the use of the compressive dressing. In embodiments, the elastomeric layer 300 provides an additional compressive force when the compressive dressing 100 is placed on the patient's head. The force may be supplemental and/or complementary to the compressive force of the matrix layer 400. In further embodiments, the elastomeric layer 300 may provide a substantially uniform compression force that it is intended to hold the compressive dressing securely on the patient's head. In this regard, the compression force(s) of the compressive dressing may be substantial enough to stop bleeding of minor lacerations and at least slow the bleeding of major lacerations while remaining secure on the patient's head. For example, the elastomeric force may be suitable to stop or slow venous bleeding, whereas the cinching force may provide additional compressive force necessary to stop or slow arterial bleeding. The elasticity of the elastomeric layer is 300 preferably such that the compressive dressing can be easily applied and removed without substantial movement of the patient during the application and removal processes.

In embodiments, the compressive dressing 100 can be applied to the patient's head while the patient is still and/or must remain still as in, for example, situations where an injury or the possibility of an injury to the neck and/or head necessitates that the position of the patient not be substantially changed.

Examples of elastomeric materials useful in the elastomeric layer 300 include, but are not limited to: rubber, polyester, spandex, and lycra.

With further reference to FIG. 2, inner layer 200 is the innermost layer of the compressive dressing and serves as the interface between the compressive dressing and the wound(s) on the patient's head. In this embodiment, the inner layer 200 preferably covers the scalp, so as to be effective against all injuries on the scalp regardless of the location of the injury on the scalp. This design allows for treatment of lacerations including lacerations not detected by practitioners at the time of application of the compressive dressing. This design further eliminates the necessity that practitioners identify and gauge the severity of particular wounds before treatment. It is often the case in the emergency treatment process that practitioners occupy critical time searching for and attempting to ascertain the severity of wounds that may be obscured by, for example, hair or blood resulting from other wounds. The compressive dressing allows for immediate treatment of head trauma, including detected and undetected wounds, while saving valuable time in the emergency treatment process. By providing an immediate introduction into the damage control and recovery phases of emergency care with minimal pre-application time, the compressive dressing combines several treatment steps and provides an efficient and effective emergency treatment tool.

The inner layer 200 and the elastomeric layer 300 may be combined into one layer. Such combined layer may have qualities similar to the qualities of the layers individually. The combined layer may be composed of any suitable material such as, for example, a carboxymethylated material with elastomeric and hemostatic properties.

An outer layer 500 may also be provided. It may provide a decorative function, such as to carry trademarks or the like. It may provide a concealing function by being opaque or translucent, to shield others from the shock of seeing a lacerated scalp. Alternatively, or in addition, it may include a transparent area or be entirely transparent to allow visualization of the scalp. It may provide a protective function, for example to protect filaments from becoming tangled or otherwise interfered with by outside objects. It may be configured to prevent further trauma to the patient's head. For example, the protective layer may be composed of a resilient and/or resistant material to protect the patient's head and/or the inner layer(s) from abrasion or puncture during emergency treatment process. Layer 500 may further have elastomeric qualities as disclosed with respect to the elastomeric layer 300.

Examples of materials that may make up the outer include, but are not limited to: plastics, nylon, and GoreTex.

The compressive dressing is not limited to the layers specified herein, and may be equipped with as many layers as appropriate to effectuate purposes described herein or conceived later in response to changing medical science.

As noted above, in embodiments, the compressive force created by the cinchable matrix layer 400 can be a greater compressive force than the compressive force generated by an elastomeric layer 300. In this manner, the cinchable matrix layer may (1) reinforce the compressive force of the elastomeric layer 300 by supplementing that force and (2) treat larger and more severe hemorrhaging that the elastomeric layer 300 is unable to effectively treat.

In embodiments, compressive dressing 100 may be capable of indicating to the practitioner the degree to which the cinchable matrix 400 need be cinched relative to the inner absorptive layer and/or elastomeric layer 300. For example, the practitioner may determine based on visual inspection or experience the severity of the injuries to the patient's head and degree to which the cinchable matrix 400 needs to be cinched alone or to supplement the force of the elastomeric layer 300, if at all. Additionally, various other indicators of the effectiveness of the elastomeric layer 300 are envisioned. For example, the inner layer 200 may be treated with chemical indicators to indicate to the practitioner the degree to which bleeding is still occurring. Each of the layers discussed herein may also be transparent to allow for visual inspection after application of the compressive dressing 100. Based on a suitable indicator, the degree to which the cinchable matrix need be cinched may be determined.

Examples of suitable materials for the chemical indicators include, but are not limited to chemical indicators for occult bleeding, the only true indicator of gross bleeding will be strikethrough blood (e.g., dressing saturation).

Figure 3:
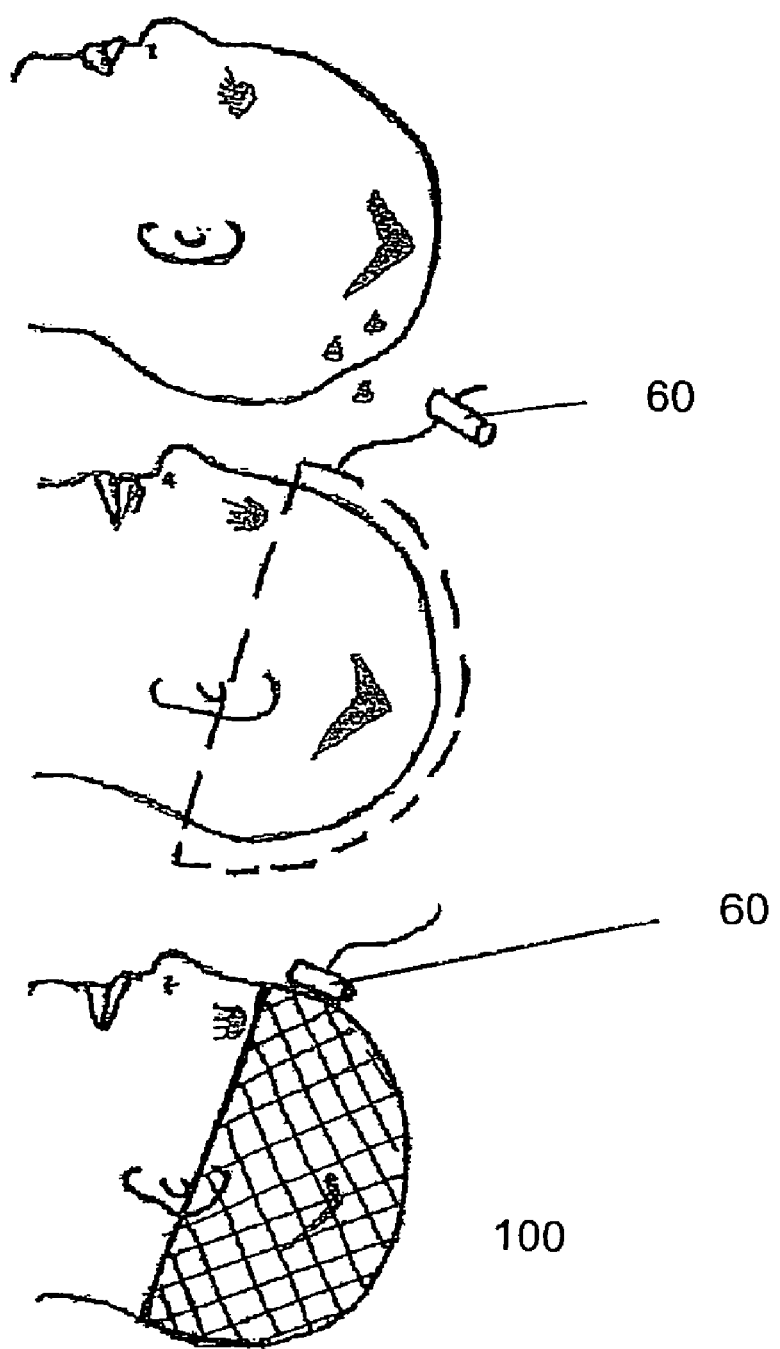
FIG. 3 illustrates a method of applying an embodiment of a compressive dressing on the head of a patient.

Compressive dressing 100 fits circumferentially around the head, as shown in FIG. 3. The perimeter filament traces the base of the compressive dressing and may provide a source, in addition to the cinching and/or elasticity of the optional elastomeric layer 300, of fixation of the cap to the patient's head. On the frontal or anterior portion of the head, the major lateral filament is preferably located just above the eye sockets, as shown in FIG. 3. On the posterior portion, the perimeter filament is preferably located below the occipital condyle, and, upon cinching by the tightener, achieves stability on the patient's head by the circumferential force acting on the perimeter filament, below the occipital condyle, to prevent the compressive dressing from slipping off of the head. On the lateral sides of the head, in embodiments, as shown in FIG. 3, the cap fits just over the ears of the patient. However, the cap may, for example, cover the ears or avoid the ears.

In exemplary embodiments, the compressive dressing is "one size fits all." The elasticity of an elastomeric layer may optionally provide a first degree of fit to the patient's head, such that the elastomeric layer 300 provides a sufficient compression force against substantially all adult head sizes. Additionally, the cinchable matrix 10 as part of the matrix layer 400 provides another degree of fit to the patient's head. The cinchability of the matrix is not particularly limited. The lateral and longitudinal filaments 30 and 40 may be of sufficient length to accommodate substantially all sizes of the head and the tightener permits cinching to fit smaller sizes.

In other embodiments, the compressive dressing may be particularly suited to certain sizes of the head. For example, the compressive dressing may be configured for certain populations, such as, for example, children or young adults. As may be readily apparent, based on generally used sizing convention, it is contemplated that the compressive dressing be developed in size ranges, such as small, medium and large or extra-large.

In exemplary embodiments, the compressive dressing is disposable. Alternatively, the compressive dressing may also be configured for repeated use. Thus, it is not necessary that all materials and costs be kept to a minimum but that the compressive dressing itself, as described herein, is generally simple and cost effective.

Additionally, the compressive dressing, while described herein as a head trauma solution of itself, may also be constructed in a manner that it complements other emergency medical treatments or devices. For example, the compressive dressing may be equipped with appropriate attachment mechanisms to attach to other body support devices, such as, for example, a cervical collar or back board. In this context, for example, it is further contemplated that the compressive dressing may be constructed with mounts for attachment or such devices on, for example, the protective layer 500 or the matrix 10 itself.

Further, while the embodiments described herein have been discussed with respect to the elasticity of various layers used to from the compressive head dressing. In other embodiments, the compressive dressing, including the layers and components described therein, is latex-free.

It should be understood that the foregoing disclosure emphasizes certain specific embodiments of the invention and that modifications or alternatives equivalent thereto are within the spirit and scope of the invention.

What is claimed is:

1. A compressive dressing for treating head trauma, comprising:
   a cinchable layer that covers at least a scalp portion of a head;
   a single opening configured to receive the head; and
   at least one tightener,
   wherein the at least one tightener is configured to allow cinching of said cinchable layer to provide a first substantially uniform compressive force over the scalp portion of the head, and
   wherein the cinchable layer includes a perimeter filament defining said opening of the compressive dressing.

2. The compressive dressing according to claim 1, further comprising a scalp contact layer located on a scalp contact side of the cinchable layer.

3. The compressive dressing according to claim 2, wherein the scalp contact layer is absorbent.

4. The compressive dressing according to claim 3, further comprising an elastomeric layer between said scalp contact layer and said cinchable layer, said elastomeric layer being configured to provide a second substantially uniform compressive force over a scalp portion of a head.

5. The compressive dressing according to claim 4, wherein the first compressive force is stronger than the second compressive force.

6. The compressive dressing according to claim 4, wherein the second compressive force is sufficient to control venous bleeding.

7. The compressive dressing according to claim 2, further comprising at least one outer layer on an opposite side of the cinchable layer from the scalp contact layer.

8. The compressive dressing according to claim 7, wherein the outer layer is configured to allow a medical practitioner to sense a degree of hemostasis achieved by the compressive dressing.

9. The compressive dressing according to claim 8, wherein the outer layer is at least partially transparent.

10. The compressive dressing according to claim 2, wherein the scalp contact layer comprises at least one hemostatic compound.

11. The compressive dressing according to claim 2, further comprising an elastomeric layer between said scalp contact layer and said cinchable layer, said elastomeric layer being configured to provide a second substantially uniform compressive force over a scalp portion of a head.

12. The compressive dressing according to claim 1, wherein the cinchable layer comprises:
at least one cinchable lateral filament; and
at least one cinchable longitudinal filament.

13. The compressive dressing according to claim 12, further comprising a major longitudinal filament, wherein the at least one lateral filament is attached to the perimeter filament and the at least one longitudinal filament is attached to the major longitudinal filament and the perimeter filament and the major longitudinal filament are cinchable at least one said tightener.

14. The compressive dressing according to claim 13, wherein the perimeter filament and the major longitudinal filament converge at the same tightener.

15. The compressive dressing according to claim 13, wherein the perimeter filament and the major longitudinal filament converge at different tighteners at different locations on the compressive dressing.

16. The compressive dressing according to claim 12, wherein the at least one lateral filament and the at least one longitudinal filament are cinchable at the same tightener.

17. The compressive dressing according to claim 12, wherein the at least one lateral filament and the at least one longitudinal filament are cinchable at different tighteners at different locations on the compressive dressing.

18. The compressive dressing according to claim 1, wherein the cinchable layer comprises at least one cinchable filament.

19. The compressive dressing according to claim 1, further comprising an elastomeric layer configured to provide a second substantially uniform compressive force over a scalp portion of a head.

20. A method for treating head trauma comprising:
covering at least a portion of a head with a compressive dressing including at least one cinchable layer comprising at least one filament and including a single opening configured to receive the head; and
cinching the at least one filament with a tightener to provide a substantially uniform compressive cinching force over the scalp,
wherein the at least one filament defines a peripheral opening of the compressive dressing.

21. The method of treating head trauma according to claim 20, further comprising applying a compressive force over the scalp with an elastomeric layer of said compressive dressing that is supplemented by said cinching force.

22. The method of treating head trauma according to claim 20, wherein the at least one filament is a plurality of filaments in the form of a matrix.

23. The method of treating head trauma according to claim 20, further comprising the step of releasing the filaments at the at least one tightener to remove the compressive dressing.

24. The method of treating head trauma according to claim 20, further comprising the step of applying a compound that promotes hemostasis of a wound to the scalp from an inner layer of said compressive dressing.

25. The method of treating head trauma according to claim 20 comprising applying a cover over the cinchable layer.

26. A compressive dressing for treating head trauma, comprising:
at least one absorbent scalp contact layer;
a single opening configured to receive a human head;
at least one elastomeric layer configured to provide a substantially uniform first compressive force to a human scalp;
a cinchable layer comprising a plurality of filaments; and
at least one tightener for cinching said plurality of filaments to provide a substantially uniform second compressive force to said scalp.

27. The compressive dressing according to claim 26, wherein the plurality of filaments includes at least one lateral filament and at least one longitudinal filament that form a matrix.

28. A compressive dressing for treating head trauma, comprising:
a cinchable layer that covers at least an upper most portion of a scalp portion of a head; and
at least one tightener,
wherein the at least one tightener is configured to allow cinching of said cinchable layer to provide a first substantially uniform compressive force over the scalp portion of the head, and
wherein the cinchable layer includes a perimeter filament defining an opening of the compressive dressing.

29. The compressive dressing according to claim 28, wherein the cinchable layer covers all of the scalp portion of the head.

30. A method for treating head trauma comprising:
covering at least a scalp portion of a head with a compressive dressing comprising an absorbent scalp contact layer, an elastomeric layer and a cinchable layer, whereby said elastomeric layer applies a first substantially uniform compressive force to said scalp through said absorbent layer; and
cinching a matrix formed by at least one lateral filament and at least one longitudinal filament in said cinchable layer at least one tightener to apply a substantially uniform additional compressive force over the scalp.

* * * * *